(12) United States Patent
Bachmann et al.

(10) Patent No.: US 6,486,110 B2
(45) Date of Patent: *Nov. 26, 2002

(54) FABRIC CARE METHOD

(75) Inventors: Frank Bachmann, Freiburg (DE); Josef Dannacher, Basel (CH); Martin Studer, Basel (CH); Beat Freiermuth, Buschwiller (FR); Cornelia Makowka, Laufenburg (DE); Peter Weingartner, Diegten (CH); Grit Richter, Neuenburg (DE); Gunther Schlingloff, Riehen (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/835,176

(22) Filed: Apr. 13, 2001

(65) Prior Publication Data

US 2001/0053755 A1 Dec. 20, 2001

Related U.S. Application Data

(63) Continuation of application No. 09/148,938, filed on Sep. 4, 1998, now abandoned.

(30) Foreign Application Priority Data

Sep. 9, 1997 (GB) ............................................. 9719009
Aug. 5, 1998 (GB) ............................................. 9816928

(51) Int. Cl.[7] ............................ C11D 3/26; C11D 3/39; C11D 3/395
(52) U.S. Cl. ................... 510/311; 510/372; 510/376; 252/186.33; 8/111; 8/137
(58) Field of Search ................................ 510/311, 372, 510/376; 8/111, 137; 252/186.33

(56) References Cited

U.S. PATENT DOCUMENTS 5,733,341 A * 3/1998 Eckhardt et al. ................. 8/111

FOREIGN PATENT DOCUMENTS

| DE | 19529905 | * 2/1997 |
|---|---|---|
| EP | 0304818 | 3/1989 |
| EP | 630964 | * 12/1994 |
| EP | 0693550 | 1/1996 |
| EP | 0717103 | 6/1996 |
| WO | 91/14694 | 10/1991 |
| WO | 95/21172 | 8/1995 |
| WO | 96/24601 | 8/1996 |
| WO | WO 97/07192 | * 2/1997 |
| WO | 97/19162 | 5/1997 |

OTHER PUBLICATIONS

Ullmann's encyclopedis, sixth edition, 1999, electronic release, chapter 1.3.2. "Agents for Use in Automatic Dishwashers" Hans–Joachim Heitland, Horst Marsen, Hans–Joachim Schlüssler.

* cited by examiner

Primary Examiner—Gregory Delcotto
(74) Attorney, Agent, or Firm—Kevin T. Mansfield

(57) ABSTRACT

The present invention provides a process for inhibiting the re-absorption of migrating dyes in the wash liquor, comprising introducing into a wash liquor containing a peroxide-containing detergent, from 0.5 to 150, preferably from 1.5 to 75, especially from 7.5 to 40 mg, per liter of wash liquor, of one or more compounds having the formula:

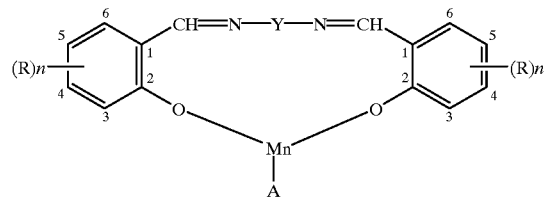

(1)

in which n is 1, 2 or 3; A is an anion;

Y is —(CH$_2$)$_m$— in which m is an integer ranging from 1 to 8; —(CH$_2$)$_p$—CH(R$_1$)— in which p is an integer ranging from 1 to 7 and R$_1$ is linear or branched C$_1$–C$_4$-alkyl, preferably methyl; —CX=CX— in which X is cyano, linear or branched C$_1$–C$_8$-alkyl or di(linear or branched C$_1$–C$_8$-alkyl)-amino;

—(CH$_2$)$_q$—NR$_1$—(CH$_2$)$_q$— in which R$_1$ has its previous significance and q is 1, 2, 3 or 4; or a 1,2-cyclohexylene residue having the formula:

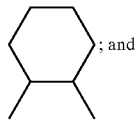

; and

R is cyano; halogen; hydroxy; OR$_1$ in which R$_1$ has its previous significance; CO$_2$R$_2$ in which R$_2$ is hydrogen or linear or branched C$_1$–C$_4$-alkyl; nitro; linear or branched C$_1$–C$_8$-alkyl;

di-(C$_4$–C$_{12}$alkyl)amino; NR$_3$R$_4$ in which R$_3$ and R$_4$ are the same or different and each is linear or branched C$_1$–C$_{12}$-alkyl; or —N$^\oplus$R$_1$R$_3$R$_4$ in which R$_1$, R$_3$ and R$_4$ have their previous significance.

12 Claims, No Drawings

FABRIC CARE METHOD

This application is a continuation of application Ser. No. 09/148,938, filed Sep. 4, 1998, now abandoned.

The present invention relates to a process for inhibiting the re-absorption of migrating dyes in the wash liquor.

It is well known that various metal compounds, e.g. manganese complexes, are useful in detergents as catalysts for oxidation with peroxygen compounds such as perborate or peroxides. It is also known that certain other manganese complexes cause enhanced bleaching effects on dirt or dyes in the wash bath. Moreover, these manganese complexes do not exhaust at all on to cotton, polyamide or polyester fibres so that the complexes cannot lead to fibre discolouration problems.

One problem associated with the evaluation of a compound as a candidate for use in a process for inhibiting the re-absorption of migrating dyes in the wash liquor, is the lack of a sufficiently reliable and comprehensive screening technique. Such a technique has now been developed and used to quantify the dye transfer inhibition performance of potential substances. This screening procedure comprises a variety of tests which makes it possible to determine the usefulness/damage balance of any candidates on a quantitative basis. A product is characterised in terms of its specific effectivity, scope of use, compatibility with the most important system components, oxygen demand and its fibre- and dyestuff degradation potential. Moreover, the precision of the data is such that structure/effect relationships can be developed. The application of the new evaluation technique to manganese complexes has resulted in the identification of further manganese complexes which exhibit excellent performance as dye transfer inhibitors, which are of relatively low molecular weight and the effectiveness of which is substantial even at low levels of addition.

Accordingly, the present invention provides a process for inhibiting the re-absorption of migrating dyes in the wash liquor, comprising introducing into a wash liquor containing a peroxide-containing detergent, from 0.5 to 150, preferably from 1.5 to 75, especially from 7.5 to 40 mg, per liter of wash liquor, of one or more compounds having the formula:

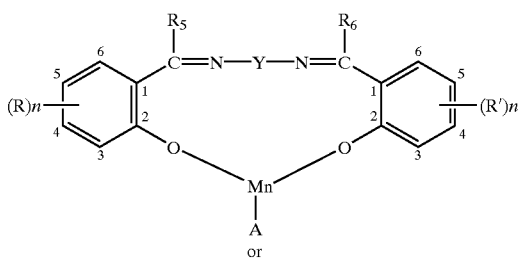

(1)

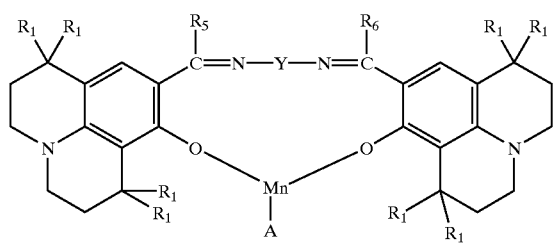

(2)

in which n is 1, 2 or 3;

A is an anion;

$R_1$ is hydrogen or $C_1$–$C_4$-alkyl,

Y is linear or branched alkylene of the formula —[$C(R_1)_2$]$_m$— in which m is an integer ranging from 1 to 8 and each $R_1$ independently from the other has its previous significance; —CX=CX— in which X is cyano, linear or branched $C_1$–$C_8$-alkyl or di(linear or branched $C_1$–$C_8$-alkyl-amino;

—$(CH_2)_q$—$NR_1(CH_2)_q$— in which $R_1$ has its previous significance and q is 1, 2, 3 or 4; or a 1,2-cyclohexylene or phenylene residue having the formula:

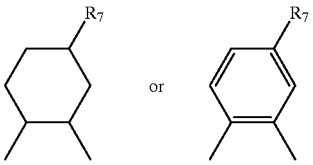

in which $R_7$ is hydrogen, $CH_2OH$ or $CH_2NH_2$ or $SO_3M$, where M is hydrogen, an alkali metal atom, ammonium or a cation formed from an amine, R and R' are each independently from the other cyano; halogen; hydroxy; $OR_1$ or $COOR_1$ in which $R_1$ has its previous significance; nitro; linear or branched partially or completely fluorinated $C_1$–$C_8$-alkyl; $NR_3R_4$ in which $R_3$ and $R_4$ are the same or different and each is hydrogen or linear or branched $C_1$–$C_{12}$-alkyl; —$N^\oplus R_1R_3R_4$ in which $R_1$, $R_3$ and $R_4$ have their previous significance or linear or branched $C_1$–$C_8$-alkylene-$R_2$ in which $R_2$ is $OR_1$, $COOR_1$ or $NR_3R_4$, $R_5$ and $R_6$ are each independently from the other hydrogen; linear or branched $C_1$–$C_4$-alkyl; unsubstituted aryl or aryl which is substituted by cyano, halogen, $OR_1$ or $COOR_1$, nitro, linear or branched $C_1$–$C_8$-alkyl, $NR_3R_4$ in which $R_3$ and $R_4$ are the same or different and each is hydrogen or linear or branched $C_1$–$C_{12}$-alkyl; —$N^\oplus R_1R_3R_4$ in which $R_1$, $R_3$ and $R_4$ have their previous significance or linear or branched $C_1$–$C_8$-alkylene-$R_2$ in which $R_2$ is $OR_1$, $COOR_1$ or $NR_3R_4$, with the proviso that each n is 1, if R and R' are both $C_1$–$C_4$-alkyl.

When Y is a 1,2-cyclohexylene residue, this residue may be in any of its cis/trans stereoisomeric forms.

Y is preferably —[$C(R_8)_2$]$_2$— wherein $R_8$ is hydrogen or methyl, —CX=CX— in which X is cyano, —$(CH_2)_q$—$NR_8$—$(CH_2)_q$— in which $R_8$ has its previous significance and q is 1, 2, 3 or 4; or a 1,2-cyclohexylene or phenylene residue having the formula:

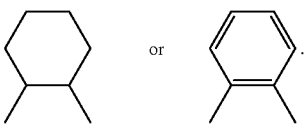

Preferred halogen atoms R or R' are chlorine, bromine and fluorine atoms.

When n is 1, preferably the group R or R' respectively is in the 4-position of the respective benzene ring, with the exceptions that when R or R' is nitro or $CO_2R_2$, the group R or R' is preferably in the 5-position of the respective benzene ring. When n is 2, preferably the groups R or R' are in the 4,6-positions of the respective benzene ring, with the exceptions that when R or R' is nitro or $CO_2R_2$ the groups R or R' are preferably in the 3,5-positions of the respective benzene ring.

When R or R' is the group di-($C_1$–$C_{12}$alkyl)amino, the alkyl moiety may be a straight- or branched chain alkyl moiety, and it preferably contains from 1 to 8, more preferably from 1 to 4 and, especially, 1 or 2 carbon atoms.

Preferred groups R and R' are dimethylamino, diethylamino, hydroxy, methoxy, ethoxy, chloro or nitro.

Anions A include halide, especially chloride, perchlorate, sulphate, nitrate, hydroxide, $BF_4^-$, $PF_6^-$, carboxylate, especially acetate, triflate or tosylate.

Some of the compounds of formula (1) and the ligands from which they are derived are known compounds. For example, in U.S. Pat. No. 5,281,578 there is described the preparation of N,N-bis(4-dimethylaminosalicylidene) diiminoethylene; in EP-A-0 693 550 there is disclosed the production of the manganese complex of N,N-bis(4-diethylaminosalicylidene)diiminoethylene; and in Bernado et.al., Inorg. Chem. 35 (2) 387 (1996), there is disclosed the production of N,N-bis(4-diethylaminosalicylidene) diiminocyclohexylene as well as the production of the manganese complex N,N-bis(4-diethylaminosalicylidenediiminocyclohexylene. New compounds of formula (1) and new ligands from which they are derived form further aspects of the present invention.

Moreover, the use, as dye transfer inhibitors, of those compounds of formula (1) in which A is an anion and a) Y is —$CH_2CH_2$— each R is di-($C_1$–$C_2$alkyl)amino; or b) Y is cyclohexylene and each R is di-($C_1$–$C_2$alkyl)amino has been broadly indicated, but not specifically described, in GB-A-2,296,015. On the other hand, the use, as dye transfer inhibitors, of those compounds of formula (1) in which A is an anion, Y is —$CH_2CH_2$— and each R is hydroxy, is believed to be completely new.

Of particular interest for use in in the method of the present invention are those compounds of formulae:

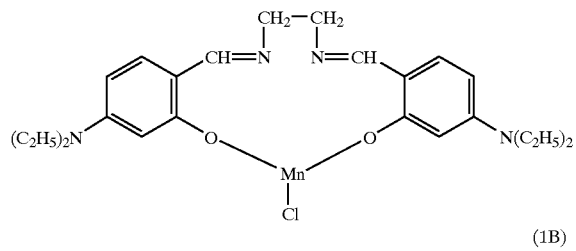

(1A)

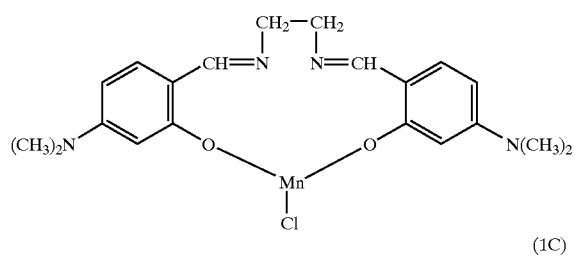

(1B)

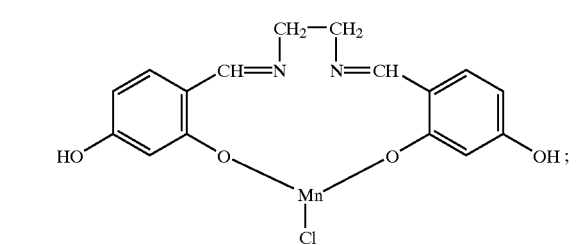

(1C)

-continued
and

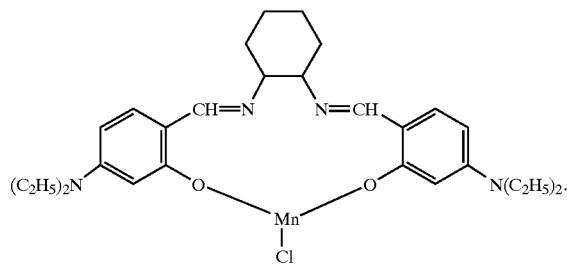

(1D)

The present invention also provides a detergent composition comprising:
i) 5–90%,preferably 5–70% of A) an anionic surfactant and/or B) a nonionic surfactant;
ii) 5–70%, preferably 5–50%, especially 5–40% of C) a builder;
iii) 0.1–30%, preferably 1–12% of D) a peroxide; and
iv) 0.005–2%, preferably 0.02–1%, especially 0.1–0.5% of E) a compound of formula (1) or (2) as defined above, each by weight, based on the total weight of the detergent.

The detergent may be formulated as a solid; or as a non-aqueous liquid detergent, containing not more than 5, preferably 0–1 wt.% of water, and based on a suspension of a builder in a non-ionic surfactant, as described, e.g., in GB-A-2158454.

Preferably, the detergent is in powder or granulate form.

Such powder or granulate forms may be produced by firstly forming a base powder by spray-drying an aqueous slurry containing all the said components, apart from the components D) and E); then adding the components D) and E) by dry-blending them into the base powder. In a further process, the component E) may be added to an aqueous slurry containing components A), B) and C), followed by spray-drying the slurry prior to dry-blending component D) into the mixture. In a still further process, component B) is not present, or is only partly present in an aqueous slurry containing components A) and C); component E) is incorporated into component B), which is then added to the spray-dried base powder; and finally component D) is dry-blended into the mixture.

The anionic surfactant component A) may be, e.g., a sulphate, sulphonate or carboxylate surfactant, or a mixture of these. Preferred sulphates are alkyl sulphates having 12–22 carbon atoms in the alkyl radical, optionally in combination with alkyl ethoxy sulphates having 10–20 carbon atoms in the alkyl radical.

Preferred sulphonates include alkyl benzene sulphonates having 9–15 carbon atoms in the alkyl radical.

In each case, the cation is preferably an alkali metal, especially sodium.

Preferred carboxylates are alkali metal sarcosinates of formula R—CO—N($R^1$)—$CH_2COOM^1$ in which R is alkyl or alkenyl having 9–17 carbon atoms in the alkyl or alkenyl radical, R' is hydrogen or $C_1$–$C_4$ alkyl and $M^1$ is alkali metal.

The nonionic surfactant component B) may be, e.g., a condensate of ethylene oxide with a $C_9$–$C_{15}$ primary alcohol having 3–8 moles of ethylene oxide per mole.

The builder component C) may be an alkali metal phosphate, especially a tripolyphosphate; a carbonate or bicarbonate, especially the sodium salts thereof; a silicate;

an aluminosilicate; a polycarboxylate; a polycarboxylic acid; an organic phosphonate; or an aminoalkylene poly (alkylene phosphonate); or a mixture of these.

Preferred silicates are crystalline layered sodium silicates of the formula $NaHSi_mO_{2m+1}\cdot pH_2O$ or $Na_2Si_mO_{2m+1}\cdot pH_2O$ in which m is a number from 1.9 to 4 and p is 0 to 20.

Preferred aluminosilicates are the commercially-available synthetic materials designated as Zeolites A, B, X, and HS, or mixtures of these. Zeolite A is preferred.

Preferred polycarboxylates include hydroxypolycarboxylates, in particular citrates, polyacrylates and their copolymers with maleic anhydride.

Preferred polycarboxylic acids include nitrilotriacetic acid and ethylene diamine tetra-acetic acid, ethylenediaminedisuccinate in racemic form as well as the enantiomeric S,S-form Preferred organic phosphonates or aminoalkylene poly (alkylene phosphonates) are alkali metal ethane 1-hydroxy diphosphonates, nitrilo trimethylene phosphonates, ethylene diamine tetra methylene phosphonates and diethylene triamine penta methylene phosphonates.

The peroxide component D) may be any organic or inorganic peroxide compound, described in the literature or available on the market, which bleaches textiles at conventional washing temperatures, e.g. temperatures in the range of from 30° C. to 90° C. In particular, the organic peroxides are, for example, monoperoxides or polyperoxides having alkyl chains of at least 3, preferably 6 to 20, carbon atoms; in particular diperoxydicarboxylates having 6 to 12 C atoms, such as diperoxyperazelates, diperoxypersebacates, diperoxyphthalates and/or diperoxydodecanedioates, especially their corresponding free acids, are of interest. It is preferred, however, to employ very active inorganic peroxides, such as persulphate, perborate and/or percarbonate. It is, of course, also possible to employ mixtures of organic and/or inorganic peroxides. Peroxides can have different crystalline forms and/or different degrees of hydration. They may be used in admixture with other organic or inorganic salts, thereby improving their stability to storage.

The addition of the peroxides to the detergent is effected, in particular, by mixing the components, for example by means of screw-metering systems and/or fluidized bed mixers.

The detergents may contain, in addition to the combination according to the invention, one or more of fluorescent whitening agents, such as a bis-triazinylamino-stilbene-disulphonic acid, a bis-triazolyl-stilbene-disulphonic acid, a bis-styryl-biphenyl, a bis-benzofuranylbiphenyl, a bis-benzoxalyl derivative, a bis-benzimidazolyl derivative, a coumarine derivative or a pyrazoline derivative; soil suspending agents, for example sodium carboxymethylcellulose; salts for adjusting the pH, for example alkali or alkaline earth metal silicates; foam regulators, for example soap; salts for adjusting the spray drying and granulating properties, for example sodium sulphate; perfumes; and also, if appropriate, antistatic and softening agents; such as smectite clays; enzymes, such as amylases; photobleaching agents; pigments; and/or shading agents. These constituents should, of course, be stable to the bleaching system employed.

A particularly preferred detergent co-additive is a polymer known to be useful in preventing the transfer of labile dyes between fabrics during the washing cycle. Preferred examples of such polymers are polyvinyl pyrrolidones, optionally modified by the inclusion of an anionic or cationic substituent, especially those having a molecular weight in the range from 5000 to 60,000, in particular from 10,00 to 50,000. Preferably, such polymer is used in an amount ranging from 0.05 to 5%, preferably 0.2–1.7% by weight, based on the weight of the detergent.

The detergents may additionally contain so-called perborate-activators, e.g. TAGU or, preferably TAED. This is preferably used in an amount of 0,05 through 5% by weight, especially 0,2 through 1,7% by weight, relative to the total weight of the detergent.

The manganese complexes of formula (2) are new compounds and some of the manganese complexes of formula (1) are new too.

The invention consequently also relates to manganese complexes of formula (3)

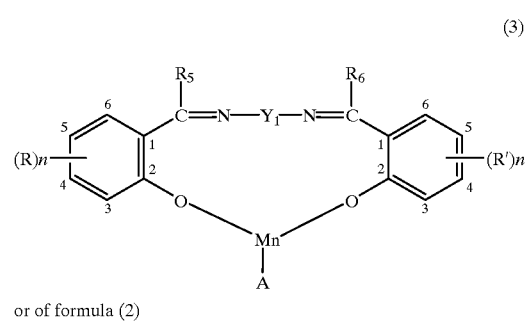

or of formula (2)

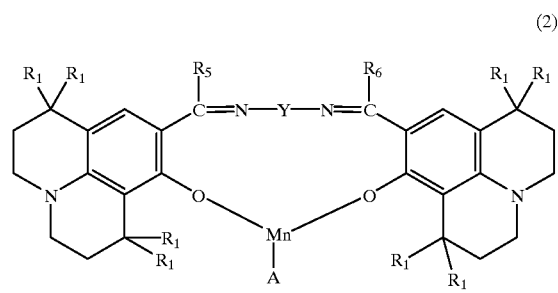

in which n is 1, 2 or 3;

A is an anion;

R and R' are each independently from the other cyano; halogen; hydroxy; $OR_1$ or $COOR_1$ in which $R_1$ has its previous significance; nitro; linear or branched partially or completely fluorinated $C_1$–$C_8$-alkyl; $NR_3R_4$ in which $R_3$ and $R_4$ are the same or different and each is hydrogen or linear or branched $C_1$–$C_{12}$-alkyl; —$N^{\oplus}R_1R_3R_4$ in which $R_1$, $R_3$ and $R_4$ have their previous significance or linear or branched $C_1$–$C_8$-alkylene-$R_2$ in which $R_2$ is $OR_1$, $COOR_1$ or $NR_3R_4$, $R_1$ is hydrogen or $C_1$–$C_4$-alkyl, $Y_1$ is —CX=CX— in which X is cyano, —$(CH_2)_q$— $NR_1$—$(CH_2)_q$— in which $R_1$ has its previous significance and q is 1, 2, 3 or 4; linear or branched alkylene of the formula —$[C(R_1)_2]_m$— in which m is an integer ranging from 1 to 8 and each $R_1$ independently from the other has its previous significance, with the proviso that at least one $R_1$ is $C_1$–$C_4$-alkyl; or a 1,2-cyclohexylene or phenylene residue having the formula:

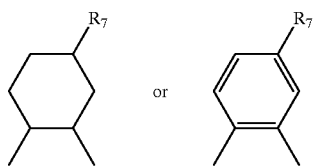

in which R$_7$ is hydrogen, CH$_2$OH or CH$_2$NH$_2$ or SO$_3$M, where M is hydrogen, an alkali metal atom, ammonium or a cation formed from an amine, with the proviso that each n is 1 if R and R' are both C$_1$–C$_4$-alkyl and Y$_1$ is an unsubstituted 1,2-cyclohexylene residue, Y is linear or branched alkylene of the formula —[C(R$_1$)$_2$]$_m$ in which m is an integer ranging from 1 to 8 and each R$_1$ independently from the other has its previous significance; —CX=CX— in which X is cyano, linear or branched C$_1$–C$_8$-alkyl or di(linear or branched C$_1$–C$_8$-alkyl)-amino;

—(CH$_2$)$_q$—NR$_1$—(CH$_2$)$_q$— in which R$_1$ has its previous significance and q is 1, 2, 3 or 4; or a 1,2-cyclohexylene or phenylene residue having the formula:

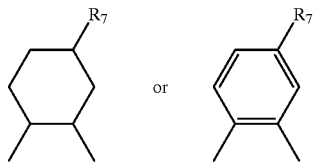

in which R$_7$ is hydrogen, CH$_2$OH or CH$_2$NH$_2$ or SO$_3$M, where M is hydrogen, an alkali metal atom, ammonium or a cation formed from an amine, R$_5$ and R$_6$ are each independently from the other hydrogen; linear or branched C$_1$–C$_4$-alkyl; unsubstituted aryl or aryl which is substituted by cyano, halogen, OR$_1$ or COOR$_1$, nitro, linear or branched C$_1$–C$_8$-alkyl, NR$_3$R$_4$ in which R$_3$ and R$_4$ are the same or different and each is hydrogen or linear or branched C$_1$–C$_{12}$-alkyl; —N$^{\oplus}$R$_1$R$_3$R$_4$ in which R$_1$, R$_3$ and R$_4$ have their previous significance or linear or branched C$_1$–C$_8$-alkylene-R$_2$ in which R$_2$ is OR$_1$, COOR$_1$ or NR$_3$R$_4$.

The ligands of formulae (4) or (5) which are contained in the manganese complexes are new themselves and these ligands are also part of the instant invention. The invention consequently also relates to compounds of the formula (4)

(4)

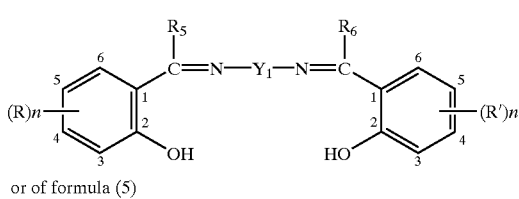

or of formula (5)

(5)

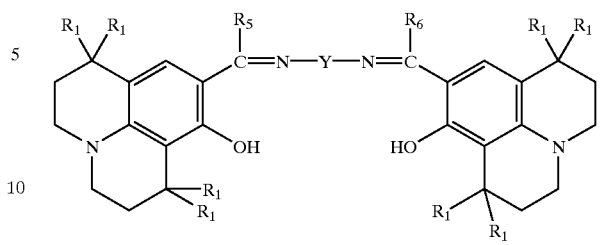

in which n is 1, 2 or 3;
R and R' are each independently from the other cyano; halogen; hydroxy; OR$_1$ or COOR$_1$ in which R$_1$ has its previous significance; nitro; linear or branched partially or completely fluorinated C$_1$–C$_8$-alkyl; NR$_3$R$_4$ in which R$_3$ and R$_4$ are the same or different and each is hydrogen or linear or branched C$_1$–C$_{12}$-alkyl; —N$^{\oplus}$R$_1$R$_3$R$_4$ in which R$_1$, R$_3$ and R$_4$ have their previous significance or linear or branched C$_1$–C$_8$-alkylene-R$_2$ in which R$_2$ is OR$_1$, COOR$_1$ or NR$_3$R$_4$, R$_1$ is hydrogen or C$_1$–C$_4$-alkyl, Y$_1$ is —CX=CX— in which X is cyano, —(CH$_2$)$_q$—NR$_1$—(CH$_2$)$_q$— in which R$_1$ has its previous significance and q is 1, 2, 3 or 4; linear or branched alkylene of the formula —[C(R$_1$)$_2$]$_m$ in which m is an integer ranging from 1 to 8 and each R$_1$ independently from the other has its previous significance, with the proviso that at least one R$_1$ is C$_1$–C$_4$-alkyl; or a 1,2-cyclohexylene or phenylene residue having the formula:

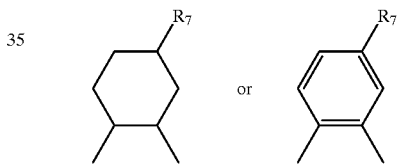

in which R$_7$ is hydrogen, CH$_2$OH or CH$_2$NH$_2$ or SO$_3$M, where M is hydrogen, an alkali metal atom, ammonium or a cation formed from an amine, with the proviso that each n is 1 if R and R' are both C$_1$–C$_4$-alkyl and Y$_1$ is an unsubstituted 1,2-cyclohexylene residue, Y is linear or branched alkylene of the formula —[C(R$_1$)$_2$]$_m$ in which m is an integer ranging from 1 to 8 and each R$_1$ independently from the other has its previous significance; —CX=CX— in which X is cyano, linear or branched C$_1$–C$_8$-alkyl or di(linear or branched C$_1$–C$_8$-alkyl)-amino;

—(CH$_2$)$_q$—NR$_1$—(CH$_2$)$_q$— in which R$_1$ has its previous significance and q is 1, 2, 3 or 4; or a 1,2-cyclohexylene or phenylene residue having the formula:

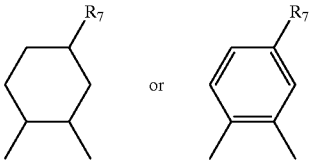

in which R$_7$ is hydrogen, CH$_2$OH or CH$_2$NH$_2$ or SO$_3$M, where M is hydrogen, an alkali metal atom, ammonium or a cation formed from an amine, $R_5$ and $R_6$ are each independently from the other hydrogen; linear or branched $C_1$–$C_4$-alkyl; unsubstituted aryl or aryl which is substituted by cyano, halogen, $OR_1$ or $COOR_1$, nitro, linear or branched $C_1$–$C_8$-alkyl, $NR_3R_4$ in which $R_3$ and $R_4$ are the same or different and each is hydrogen or linear or branched $C_1$–$C_{12}$-alkyl; —$N^\oplus R_1R_3R_4$ in which $R_1$, $R_3$ and $R_4$ have their previous significance or linear or branched $C_1$–$C_8$-alkylene-$R_2$ in which $R_2$ is $OR_1$, $COOR_1$ or $NR_3R_4$.

Preferred compounds of formula (4) are the following:

(2a)

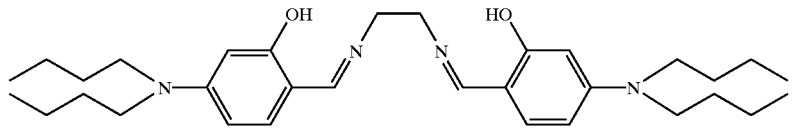

(2b)

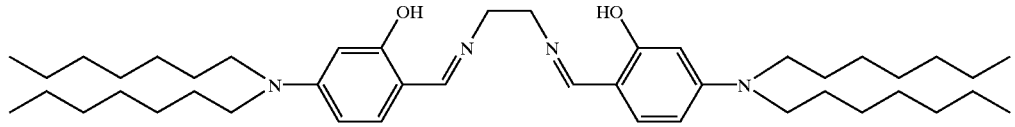

(2c)

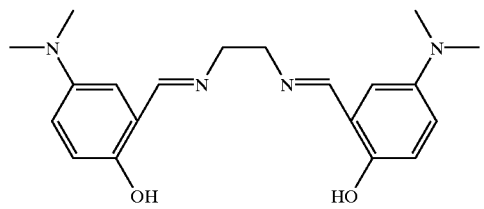

(2d)

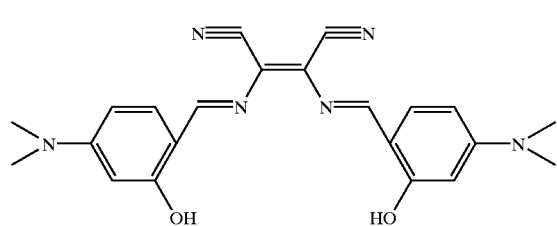

(2e)

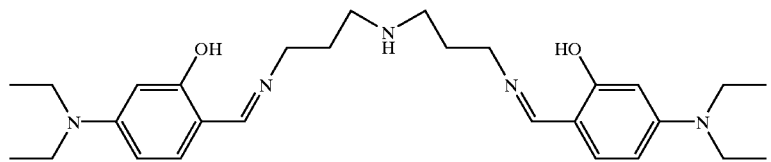

(2f)

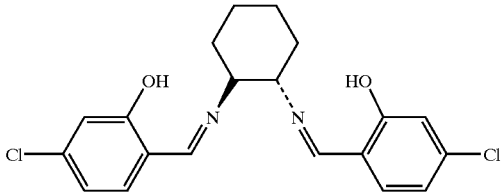

2g

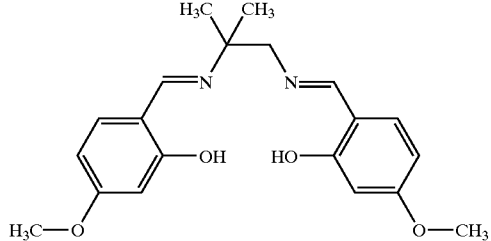

2h

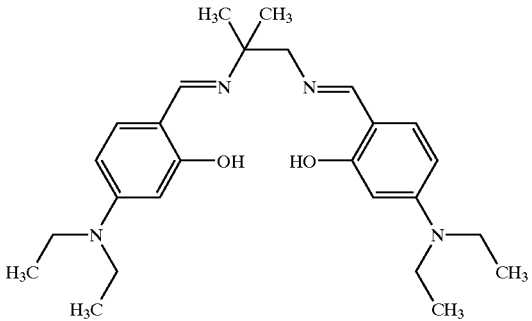

2i

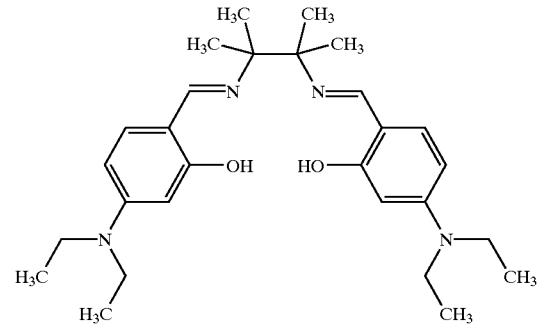

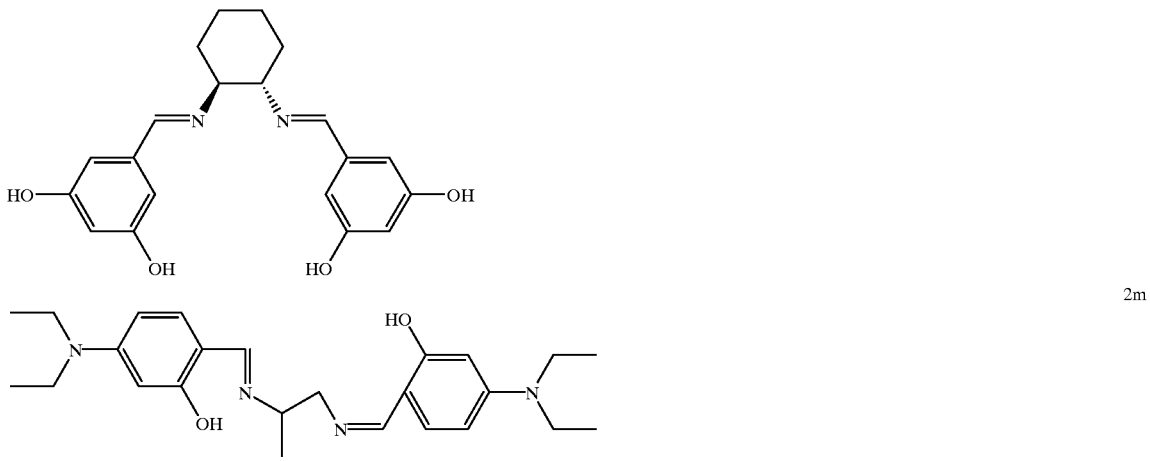

Preferred compounds of formula (5) are

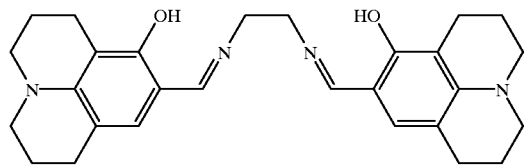

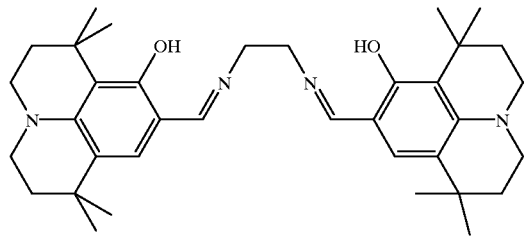

The following Examples serve to illustrate the invention; parts and percentages are by weight, unless otherwise stated.

Preparation of the New Ligands

Ligand 2a a) Preparation of the corresponding aldehyde

Firstly, the starting compound N,N-dibutyl-4-amino-2-hydroxy-benzaldehyde had to be prepared by Vilsmeyer formylation of N,N-dibutyl-3-amino-phenol. The Vilsmeyer reagent was prepared by slow addition of 4.7 ml (0.0497 mol) of phosphorus oxychloride to 15 ml (0.189 mol) of N,N-dimethyl formamide with stirring for 15 minutes at room temperature. Stirring was continued for 30 more minutes before this Vilsmeyer reagent was used. 11 g (0.497 mol) N,N-dibutyl-3-amino-phenol, prepared by alkylation of 3-aminophenol after the procedure described in EP 0356173 was dissolved in 13 ml N,N-dimethyl formamide. This solution was added dropwise at room temperature to the Vilsmeyer reagent described above. The solution was stirred for 3 h, heated to 50° C. for 10 minutes. The solution was cooled to room temperature and stirred for another 2 h. Then, the reaction mixture was poured onto 70 g ice and stirred for 1 h. The aequous layer was extracted three times with 100 ml chloroform. The combined organic layers were evaporated in vacuo. The raw product was purified by column chromatography (450 g silicagel, eluent hexane/ethyl acetate 15:1, vol. ratio). 3.2 g (26%) N,N-Dibutyl-4-amino-2-hydroxy-benzaldehyde was obtained as an orange oily compound.

b) Preparation of the ligand 2a

To a solution of 1 g (0.004 mol) 4 N,N-dibutyl-4-amino-2-hydroxy-benzaldehyde in 2 ml ethanol at 55° C. were added dropwise 0.13 ml (0.00191 mol) of ethylene diamine. The resulting clear solution was kept under stirring for 4 h between 60–65° C. The solution was cooled and the precipitate formed was filtered and dried to give 540 mg (54%) of a slightly brownish solid.

$^{13}$C NMR (CDCl$_3$): δ=14.0 (aliph. CH$_3$), 20.2, 29.5, 50.8, 58.2 (aliph. CH$_2$), 98.2, 103.1, 132.9 (tert. Aryl-C), 108.2, 151.8, 165.7 (quart Aryl-C), 164.3 (C̲=N).

Calc. C 73.52 H 9.65 N 10.72
Found C 73.14 H 9.34 N 10.55

Ligand 2b

Preparation of the corresponding aldehyde:

A solution of 13 g (0.04255 mol) of N,N-heptyl-3-amino-phenol, prepared after the procedure described in EP 0356173, in 30 ml chloroform was treated with 6.7 g (0.04255 mol) of phosphorus oxychloride and 12.4 g (0.169 mol) of N,N-dimethyl formamide and worked-up as described for compound 2a. Purification was accomplished by column chromatography a mixture of chlorobenzene/ethyl acetate/ethanol (90:5:5, vol. ratio). 1.78 g (13%) of N,N-heptyl-4-amino-2-hydroxy-benzaldehyde was obtained as a green oily compound.

A solution of 0.8 g (0.0024 mol) N,N-heptyl-4-amino-2-hydroxy-benzaldehyde in 1 ml ethanol was treated and worked-up as described for compound 2a. 720 mg (91%) of the ligand was obtained as a brown oil which slowly crystallized when stored at 5° C. for three days.

$^{13}$C NMR (CDCl$_3$): δ=14.1 aliph. CH$_3$), 22.6, 27.1, 27.5, 29.2, 31.9, 51.0, 57.7 (aliph. CH$_2$), 98.3, 103.2, 133.0 (tert. Aryl-C), 108.2, 152.1, 166.5 (quart Aryl-C), 164.2 (C̲=N).

Calc. C 76.47 H 10.79 N 8.11
Found C 76.18 H 10.60 N 7.95

Ligand 2c

To a stirred solution of 2 g (0.0121 mol) of 5-dimethylamino-2-hydroxy-benzaldehyde [prepared after

*Bull. Chem. Soc. Jpn.* 51 (1978) 2433] in 6 ml ethanol at 50° C. was added dropwise 0.35 g (0.0058 mol) of ethylene diamine. An orange suspension was formed which was stirred at 60° C. for 4 h. The suspension was cooled to room temperature, filtered and dried in vacuo at 30° C. The pure ligand was obtained as a yellow solid (1.77 g, 87%).

$^{13}$C NMR (CDCl$_3$): δ=45.0 (aliph. NCH$_3$), 60.0 (aliph. CH$_2$), 116.2, 117.2, 119.6 (tert. Aryl-C), 118.4, 144.2, 153.3 (quart Aryl-C), 166.8 (C=N).

Calc. C 67.77 H 7.39 N 15.81

Found C 67.56 H 7.35 N 15.25

Ligand 2d

To a solution of 2.5 g (0.015 mol) N,N-dimethyl-4-amino-2-hydroxy-benzaldehyde in 7 ml ethanol was added within 2 minutes a solution of 0.82 g (0.00721 mol) of diamino maleic acid dinitrile in 14 ml methanol. The reaction mixture was heated for 5 h at 65° C. A brown suspension was obtained which was cooled, filtered and dried to give a brown solid (2.03 g, 70%).

$^{13}$C NMR (CDCl$_3$): δ=40.0 (aliph. NCH$_3$), 110.4, 115.1 (aliph. quart. C), 98.2, 105.8, 133.0 (tert. Aryl-C), 110.4, 115.1, 161.2 (quart Aryl-C), 156.2 (C=N).

Ligand 2e

A solution of 5.0 g (0.0259 mol) 4-diethylamino-2-hydroxy-benzaldehyde in 12 ml ethanol was treated with 1.66 g (0.0123 mol) of bis-(3-aminopropyl)amine and worked-up as described for ligand 2a. The raw product was dried in high vacuo to give 5.7 g (98%) of a red oil.

$^{13}$C NMR (CDCl$_3$): δ=12.8 (aliph. CH$_3$), 31.1, 44.5, 47.2, 53.6 (aliph. CH$_2$), 98.7, 103.1, 133.2 (tert. Aryl-C), 108.2, 152.2, 169.0 (quart Aryl-C), 162.5 (C=N).

Calc. C 68.77 H 9.00 N 14.32.

Found C 67.09 H 8.66 N 13.38 (Substance contains 1.51% water)

Ligand 2f

A solution of 0.81 g (0.00517 mol) 4-chloro-2-hydroxy-benzaldehyde prepared after Beilstein (E IV, vol. 8, 223) in 2.5 ml ethanol was treated with 0.29 g (0.00246 mol) trans-1,2-diaminohexane and worked-up as described for ligand 2a. The ligand was obtained as a yellow oil (0.96 g, 100%) which upon standing slowly crystallized.

$^{13}$NMR (CDCl$_3$): δ=24.1, 32.9 (CH$_2$), 54.6, 72.4 (CH), 117.0, 138.1, 162.0 (quart Aryl-C), 117.2, 118.9 (tert. Aryl-C), 164.0(C=N).

Calc. C 61.39 H 5.15 N 7.16 Cl 18.12

Found C 61.50 H 5.34 N 7.70 Cl 17.26

Ligand 2g

To a stirred solution of 2 g (0.013 mol) 2-hydroxy-4-methoxy-benzaldehyde in 10 ml ethanol at room temperature were added at once 579 mg (0.0065 mol) 1,2-diethylamino-2-methylpropane. The solution was heated at 60° C. for 3 h and cooled to room temperature.

The clear solution was evaporated and dried in high vacuo to give the ligand as a red-brown oil (2.58 g, 100%).

$^{13}$C NMR (CDCl$_3$): δ=25.3((CH$_3$)$_2$C—), 55.3 (OCH$_3$), 59.2 (aliph, quart. C), 69.2 (NCH$_2$), 101.2, 101.4 (tert. Aryl-C), 106.3, 106.4 (tert. Aryl-C), 112.2, 112.3 (quart Aryl-C), 132.9, 133.1 (tert. Aryl-C), 160.3, 165.6 (C=N), 163.7, 163.9 (quart. Aryl-C), 165.0, 166.7 (quart. Aryl-C).

Calc. C 67.39 H 6.79 N 7.86

Found C 67.51 H 6.91 N 7.69

Ligand 2h 2 g (0.0103 mol) 4-diethylamino-2-hydroxy-benzaldehyde and 456 mg (0.00517 mol) 1,2-diethylamino-2-methylpropane were treated and worked-up as described for ligand 2g. The ligand was obtained as a red-brown solid (1.9 g, 84%).

$^{13}$C NMR (CDCl$_3$): δ=12.7 (CH$_3$CH$_2$N), 25.4 ((CH$_3$)$_2$C—), 44.4 (NCH$_2$CH$_3$), 58.4 (quart. C), 68.6 (NCH$_2$), 98.1, 98.6 (tert. Aryl-C), 103.0, 103.1 (tert. Aryl-C), 108.3, 108.4 (quart Aryl-C), 133.1, 133.4 (tert. Aryl-C), 151.6, 151.9 (quart. Aryl-C), 158.9, 164.5 (C=N), 166.0, 168.4 (quart. Aryl-C).

Calc. C 71.91 H 8.74 N 12.72

Found C 70.88 H 8.65 N 12.35

Ligand 2i 1.21 g (0.006 mol) 4-diethylamino-2-hydroxy-benzaldehyde was dissolved under stirring in 2 ml ethanol at 50° C. At this temperature, a solution of 2,3-diamino-2,3-dimethyl-butane (prepared after Beilstein E IV, vol. 4, 1354) in 2 ml ethanol was added within 30 minutes. The reaction mixture was heated to 70 C. for 3 h and stirred at room temperature for another 8 h. The resulting suspension was filtered and the precipitate was washed with cold ethanol and dried in high vacuo to give a brown solid (890 mg, 66%).

$^{13}$C NMR (CDCl$_3$): δ=12.8, 23.0 (CH$_3$), 44.5 (CH$_2$), 63.3 (quart. alipht. C), 98.6, 103.0, 133.5 (tert. Aryl-C), 108.2, 152.1, 169.1 (quart. Aryl-C), 158.9 (C=N).

Calc. C 72.07 H 9.07 N 12.01

Found C 71.78 H 9.03 N 11.88

Ligand 2j

To a solution of 974 mg (0.0045 mol) 2,3,6,7-tetrahydro-8-hydroxy-1H,5H-benzo[ij]quinolizine-9-carboxaldehyde in 30 ml methanol was added a solution of 148 mg (0.0025 mol) ethylene diamine. The reaction mixture was heated under reflux for 1 h. The formed precipitate was filtered and crystallized in 100 ml of methanol to yield 590 mg (29%) of yellow crystals.

$^{13}$C NMR (CDCl$_3$): δ=20.4, 21.3, 22.2, 27.2, 49.8, 50.1, 58.2 (CH$_2$), 106.8, 107,9, 112,2, 129.0, 146.4, 164.3 (C=N).

Calc. C 73.33 H 7.47 N 12.22

Found C 73.37 H 7.54 N 12.22

Ligand 2k

A solution of 1.95 g (0.00714 mol) 8-hydroxy-1,1,7,7-tetramethyljulolidine-9-carboxaldehyde in 60 ml methanol was reacted with 236 mg (0.0393 mmol) ethylene diamine as described for ligand 2j. The precipitate was filtered and washed with methanol to give 1.52 g (75%).

$^{13}$C NMR (CDCl$_3$): δ=28.5 (prim. C), 31.2 (prim. C), 31.7, 32.2, 36.6, 40.1, 47.0, 47.4, 58.9, 108.7, 114.8, 121.6, 127.5), 145.7, 161.2, 165.4 (C=N).

Ligand 2l

A solution of 5.0 g (0.0355 mol) 2,4-dihydroxy-benzaldehyde in 17 ml ethanol was treated with 1.97 g (0.0169 mol) of trans-1,2-diaminocylohexane and heated at 65° C. for 5 h. A yellow suspension was formed which was cooled to 2° C. The precipitate was filtered, washed with ethanol and dried to give 5.9 g (99%) of a yellow solid.

$^{13}$C NMR (DMSO-$d_6$): δ=24.9, 33.6 (CH$_2$), 71.3 (CH), 103.3, 107.8, 134.1 (tert. Aryl-C), 112.0, 162.6 (quart. Aryl-C), 164.9 (C=N)

$^{13}$C NMR (CDCl$_3$): δ=12.7, 20.3 (CH$_3$), 44.5, 63.8 (CH$_2$), 98.2, 103.1, 133.1 (tert. Aryl-C), 108.3, 151.5, 165.5 (quart. Aryl-C), 162.5 (C=N)

The following ligands are known compounds.

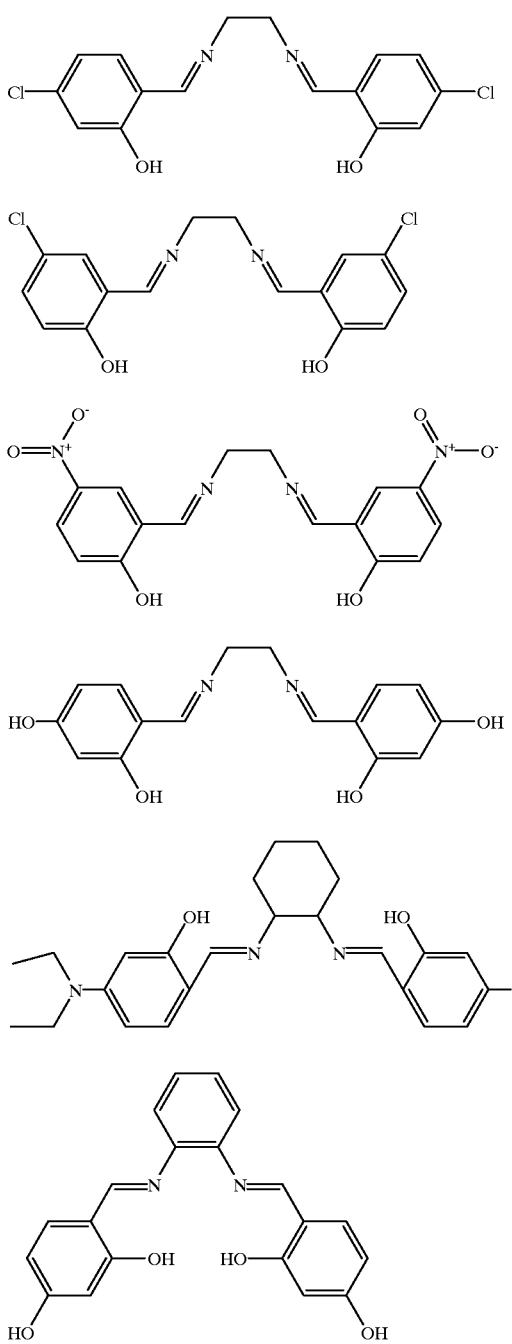
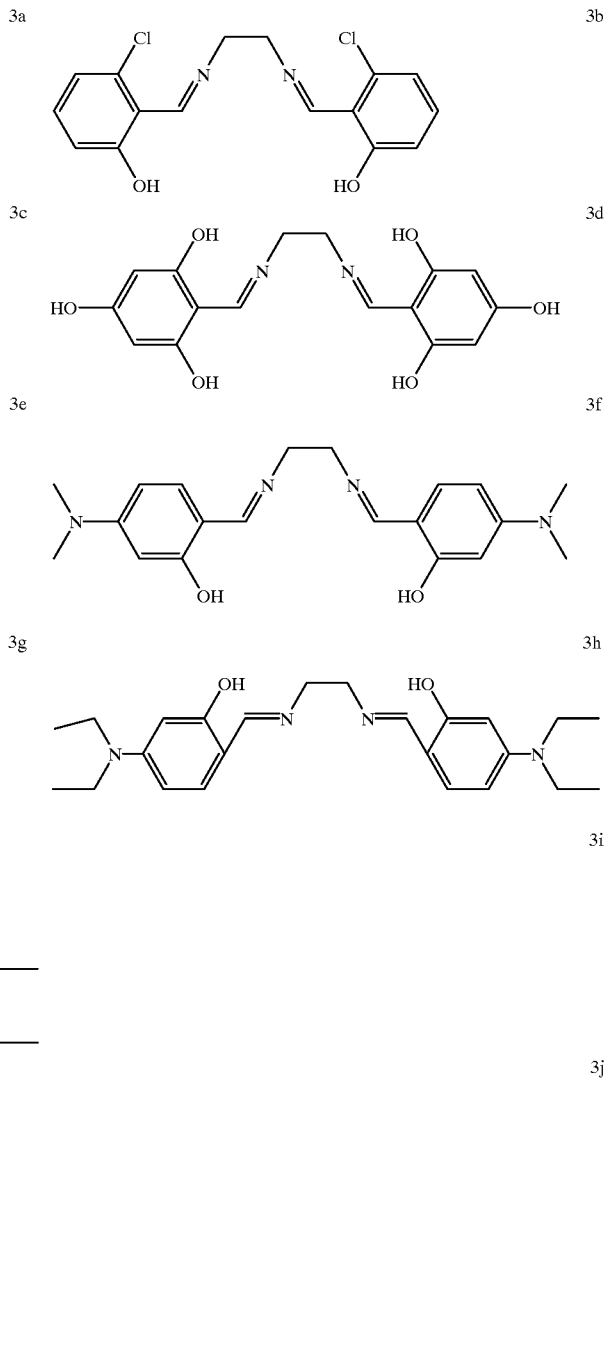

Ligand 2m

A solution of 5 g (0.025 mol) 4-diethylamino-2-hydroxy-benzaldehyde in 12 ml ethanol was treated with 0.92 g (0.0123 mol) of 1,2-diaminopropane and heated at 65° C. for 5 h. The solution was cooled and stirred for 8 h. The solution was concentrated to give 4.68 g (90%) of a brown solid.

These ligands were prepared according to known literature procedures:

All described ligands were transformed into its manganese complexes. The syntheses of these complexes were performed according to the literature as described by E. N. Jacobsen et al. J. Org. Chem., 59 (1994) 1939 or in Patent GB-A-2,296,015. As an example for the standard procedure, the synthesis of the manganese complex 1b is described: To a stirred solution of 667 mg of ligand 3f dissolved in 10 ml of ethanol was added 465 mg manganese-II-acetate-tetrahydrate. The reaction solution was heated at 65–70° C. for 4 h. Afterwards, the solution was evaporated and the residue was dissolved in 40 ml of water. The solution were treated with 3.7 g of sodium chloride. The resulting precipitate was filtered and dried in vacuo. The manganese complex was obtained as red-brown powder (820 mg, 86%).

EXAMPLE 1

Each of the test compounds is then evaluated to determine its activity as a dye transfer inhibitor according to the following method.

7.5 g of white cotton are washed in 80 ml of wash liquor. The wash liquor contains 8.6 mmol/l $H_2O_2$, a solution of a test dyestuff and 7.5 g/l of the standard detergent ECE phosphate-free (456 IEC) EMPA, Switzerland:

| | |
|---|---|
| 9.74% | Sodium linear alkylbenzenesulfonate (Marion A375); |
| 5.19% | Ethoxylated $C_{12}$–$C_{18}$ fatty alcohol (7 moles EO); |
| 3.64% | Sodium soap; |
| 6.49% | Silicon foam inhibitor; |
| 32.47% | Sodium aluminium silicate Zeolite 4A; |
| 11.82% | Sodium carbonate; |
| 5.19% | Sodium salt of acrylic acid/maleic acid copolymer (Sokolan CP 5) |
| 3.38% | Sodium silicate ($SiO_2:Na_2O$ = 3.3:1); |
| 1.30% | Carboxymethylcellulose |
| 0.26% | EDTA; |
| 7.40% | Sodium sulfate; |
| 12.21% | Water; |
| 0.65% | Proteolytic enzyme prills; |
| 0.26% | Fluorescent whitening agent; |
| 20.0% | Sodium percarbonate; and |
| 3.0% | TAED. |

The washing is conducted in beakers in a LINITEST apparatus at 40° C. over 30 minutes. The test dye transfer inhibitor is added at a level of 50 μmol/l. The commercially available test dye used is either Cuprophenyl Brown 2GL (Dye 1) used at a level of 10 mg/l of the 250% formulation, or Reactive Blue 238 (Dye 2) used at a level of 6 mg/l of the 100% formulation. The reflection spectra of the respective test samples are measured with a SPECTRAFLASH 2000 instrument and are transformed into brightness values according to the CIE standard procedure.

The percentage DTI (dye transfer inhibition) effectivity (a) is then calculated in accordance with the following equation:

$$a = \{[Y(E)-Y(A)]/[Y(W)-Y(A)]\} \times 100$$

in which Y(W), Y(A) and Y(E), respectively, are the CIE-brightness values of the white material before treatment, of the fabric as obtained when washed without a dye transfer inhibitor and of the fabric as obtained when washed with a dye transfer inhibitor. A zero percent value for the a-value denotes a completely ineffective dye transfer inhibitor, that is a compound, the addition of which to a wash liquor allows full dye transfer on to the white material. By contrast, a 100 percent value for a denotes a perfect dye transfer inhibitor, that is a compound, the addition of which to a wash liquor allows no dye transfer on to the white material.

The results obtained are set out in the following Table 1.

TABLE 1

| | DTI effectivity (a) | |
|---|---|---|
| Test dye transfer inhibitor | Dye 1 | Dye 2 |
| inhibitor 1(A) | 90 | 98 |
| inhibitor 1(B) | 82 | 87 |
| inhibitor 1(C) | 80 | 85 |
| inhibitor 1(D) | 84 | 86 |
| Manganese complexes of ligand | | |
| 2a | 71 | |
| 2b | 78 | |
| 2c | 70 | |
| 2d | 73 | |
| 2e | 68 | |
| 2f | 84 | |
| 2g | 80 | |
| 2h | 87 | |
| 2i | 69 | |
| 2j | 90 | |
| 2k | 77 | |
| 2l | 85 | |
| 2m | 85 | |

TABLE 1b

DTI-effiency of manganese complexes derived from known ligands

| Test dye transfer inhibitor | DTI effectivity (a) |
|---|---|
| 3a | 92 |
| 3b | 74 |
| 3c | 76 |
| 3d | 61 |
| 3e | 78 |
| 3f (Ligand for Mn complex 1b) | cf. TABLE 1 |
| 3g (Ligand for Mn complex 1c) | " |
| 3h (Ligand for Mn complex 1a) | " |
| 3l (Ligand for Mn complex 1d) | " |
| 3j | 97 |

The results in Table 1 clearly demonstrate that claimed manganese complexes exhibit excellent performance as dye transfer inhibitors.

EXAMPLE 2

The procedure in Example 1 is repeated with the exceptions that only inhibitors 1(A) and 1(B) are used and that the amounts used of these inhibitors are varied over a wide range.

The results obtained are set out in the following Table 2.

TABLE 2

| Test dye transfer inhibitor | Concentration μmol/l | DTI effectivity (a) | |
|---|---|---|---|
| | | Dye 1 | Dye 2 |
| inhibitor 1(A) | 5 | 59 | 64 |
| | 10 | 69 | 85 |
| | 20 | 83 | 95 |
| | 30 | 90 | 103 |
| | 50 | 90 | 98 |
| | 70 | 98 | 105 |
| inhibitor 1(B) | 5 | 50 | 43 |
| | 10 | 61 | 76 |
| | 20 | 76 | 78 |
| | 30 | 77 | 78 |

TABLE 2-continued

| Test dye transfer | | DTI effectivity (a) | |
|---|---|---|---|
| inhibitor | Concentration μmol/l | Dye 1 | Dye 2 |
| | 50 | 82 | 87 |
| | 70 | 82 | 88 |

The results in Table 2 show that manganese complexes of formula (1) exhibit excellent performance as dye transfer inhibitors even at very low levels of addition.

EXAMPLE 3

The procedure in Example 1 is repeated with the exceptions that only inhibitors 1(A) and 1(B) are used and that their effectiveness in controlling transfer of a wide range of dyes, at various levels of dye addition, is examined. The results obtained are set out in the following Table 3.

TABLE 3

| | | DTI effectivity (a) | |
|---|---|---|---|
| Test dye | Concentration μmol/l | inhibitor 1(A) | inhibitor 1(B) |
| Cuprophenyl Brown 2GL 250% | 10 | 90 | 82 |
| Reactive Blue 238 100% | 6 | 98 | 87 |
| Reactive Black 5 133% | 12 | 80 | 65 |
| Direct Black 22 400% | 6 | 76 | 73 |
| Reactive Blue 19 Special 100% | 20 | 97 | 88 |
| Acid Blue 113 180% | 6 | 96 | 90 |
| Disperse Violet 1 100% | 6 | 90 | 72 |

The results in Table 3 show that manganese complexes of formula (1) exhibit excellent performance as dye transfer inhibitors against migration of a a wide range of dyes, at various levels of dye addition.

EXAMPLE 4

The procedure in Example 1 is repeated for a washing temperature of 20° C.

The results obtained are set out in the following Table 4.

TABLE 4

| | DTI effectivity (a) | |
|---|---|---|
| Test dye transfer inhibitor | Dye 1 | Dye 2 |
| inhibitor 1(A) | 82 | 86 |
| inhibitor 1(B) | 79 | 73 |
| inhibitor 1(C) | 70 | 86 |
| inhibitor 1(D) | 80 | 80 |

The results in Table 4 show that manganese complexes of formula (1) exhibit excellent performance as dye transfer inhibitors even at washing temperatures as low as 20° C.

EXAMPLE 5

The procedure in Example 1 is repeated with the exceptions that only inhibitors 1(A) and 1(B) are used and that the detergent composition used is modified by the addition of 4% by weight of TAED, as bleach activator.

The results obtained are set out in the following Table 5.

TABLE 5

| | DTI effectivity (a) | |
|---|---|---|
| Test dye transfer inhibitor | Dye 1 | Dye 2 |
| inhibitor 1(A) | 99 | 100 |
| inhibitor 1(B) | 96 | 97 |

The results in Table 5 show that manganese complexes of formula (1) exhibit excellent performance as dye transfer inhibitors and that their effectiveness is not impaired by their co-use with activated bleach systems.

Moreover, the compatibility between manganese complexes of formula (1) and activated bleach systems has recriprocal benefits. In particular, under the conditions described in Example 1, the bleach-promoting action of TAED is maintained, even in the presence of 20 μM of a manganese complex of formula (1). Thus, the brightness increase (ΔY) obtained with tea-stained cotton test material is 24 when no dye transfer inhibitor is present (control test); 23 using inhibitor 1(A); and 24 using inhibitor 1(B).

EXAMPLE 6

The procedure in Example 1 is repeated with the exceptions that only inhibitors 1(A) and 1(B) are used and that the detergent composition used is modified by the addition of 100 μM of DEQUEST 2041 [ethylenediamine-tetra-(methylenephosphonic acid)], as sequestering agent.

The results obtained are set out in the following Table 6.

TABLE 6

| | DTI effectivity (a) | | | |
|---|---|---|---|---|
| | Dye 1 | | Dye 2 | |
| Test dye transfer inhibitor | 20 μmol/l | 50 μmol/l | 20 μmol/l | 50 μmol/l |
| inhibitor 1(A) without DEQUEST | 83 | 90 | 95 | 98 |

TABLE 6-continued

| | DTI effectivity (a) | | | |
|---|---|---|---|---|
| Test dye transfer inhibitor | Dye 1 | | Dye 2 | |
| with DEQUEST inhibitor 1(B) | 89 20 µmol/l | 93 50 µmol/l | 95 20 µmol/l | 98 50 µmol/l |
| without DEQUEST | 76 | 82 | 78 | 87 |
| with DEQUEST | 82 | 87 | 79 | 83 |

The results in Table 6 show that manganese complexes of formula (1) exhibit excellent performance as dye transfer inhibitors and that their effectiveness is not impaired by their co-use with a sequestering agent. Sequestering agents are usually present in detergent formulations and their presence can often lead to the observation of higher a-values. This is because heavy metal ions are masked, and therefore the reservoir of peroxidic oxygen is not depleted by useless degradation processes.

EXAMPLE 7

The procedure in Example 1 is repeated with the exceptions that only inhibitors 1(A) and 1(B) are used and that the amounts used of $H_2O_2$ in the detergent are varied.

The results obtained are set out in the following Table 7.

| | DTI effectivity (a) | | | |
|---|---|---|---|---|
| | inhibitor 1(A) | | inhibitor 1(B) | |
| $H_2O_2$ Concentration µmol/l | Dye 1 | Dye 2 | Dye 1 | Dye 2 |
| 2.1 | 84 | 85 | 65 | 60 |
| 4.3 | 86 | 88 | 83 | 79 |
| 8.6 | 89 | 89 | 85 | 82 |

The results in Table 7 show that, even when the conventional amount of $H_2O_2$ present in the detergent formulation is reduced by a factor of 4, the effectiveness of manganese complexes of formula (1) as dye transfer inhibitors is retained.

EXAMPLE 8

The procedure in Example 1 is repeated with the exceptions that only inhibitors 1(A) and 1(B) are used and that a series of dyed cotton fabrics is used which are known to very sensitive to aggressive bleaching systems. For the purpose of comparison, an analogous test using TAED instead of inhibitor 1(A) or 1(B) is conducted. The washing treatment is carried out five times with each respective detergent composition and, after completion of the fifth respective wash, the percentage loss of dye is determined.

The results are set out in the following Table 8.

TABLE 8

| | % Dyestuff Loss | | |
|---|---|---|---|
| Test Dye | inhibitor 1(A) | inhibitor 1(B) | TAED |
| Reactive Brown 017 | 16 | 17 | 15 |
| Vat Brown 001 | 0 | 4 | 2 |

TABLE 8-continued

| | % Dyestuff Loss | | |
|---|---|---|---|
| Test Dye | inhibitor 1(A) | inhibitor 1(B) | TAED |
| Reactive Red 123 | 16 | 10 | 13 |
| Direct Blue 085 | 18 | 14 | 14 |

The results in Table 8 show that the dyestuff loss observed when using a detergent containing a manganese complex of formula (1) as dye transfer inhibitor, is of the same order as that experienced when a detergent containing a TAED-activated bleach system is used. The latter detergent composition represents the state of the art for oxygen bleaches, and its dye damage/usefulness balance is accepted in the industry.

Using the same test conditions, after completion of the fifth respective wash, the percentage relative reduction of DP (average degree of polymerisation) is determined, in order to assess the damage to the fibre.

The results are set out in the following Table 9.

TABLE 9

| | % Relative DP-Reduction | | |
|---|---|---|---|
| Test Dye | inhibitor 1(A) | inhibitor 1(B) | TAED |
| Reactive Brown 017 | 4 | 12 | 5 |
| Vat Brown 001 | 18 | 20 | 19 |
| Reactive Red 123 | 26 | 19 | 7 |
| Direct Blue 085 | 0 | 1 | 2 |

The results in Table 9 show that the fibre damage on dyed cotton material observed when using a detergent containing a manganese complex of formula (1) as dye transfer inhibitor, is of the same order as that experienced when a detergent containing a TAED-activated bleach system is used.

What is claimed is:

1. A process which inhibits the re-absorption of migrating dyes in a wash liquor, comprising introducing into a wash liquor containing a peroxide-containing detergent, from 0.5 to 150 mg, per litre of wash liquor, one or more symmetrical compounds having the formula:

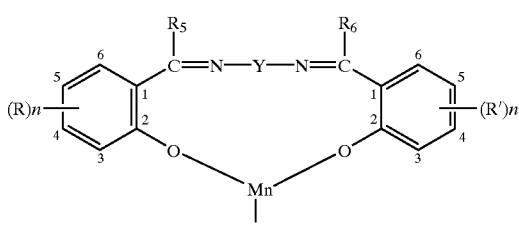

or one or more compounds having the formula:

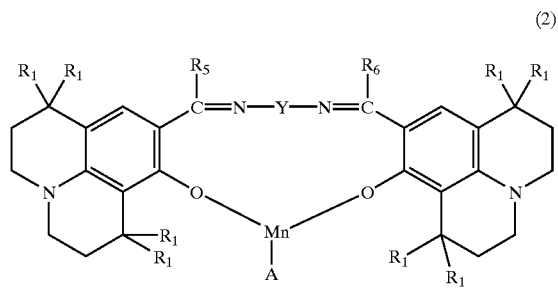

in which n is 1, 2 or 3;

A is an anion;

$R_1$ is hydrogen or $C_1$–$C_4$-alkyl,

Y is linear or branched alkylene of the formula —[C($R_1$)$_2$]$_m$ in which m is an integer ranging from 1 to 8 and each $R_1$ independently from the others has its previous significance; —CX=CX— in which X is cyano, linear or branched $C_1$–$C_8$-alkyl or di(linear or branched $C_1$–$C_8$-alkyl-amino; —(CH$_2$)$_q$—NR$_1$—(CH$_2$)$_q$— in which $R_1$ has its previous significance and q is 1, 2, 3 or 4; or a 1,2-cyclohexylene or phenylene residue having the formula:

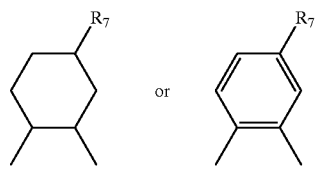

in which $R_7$ is hydrogen, CH$_2$OH or CH$_2$NH$_2$ or SO$_3$M, where M is hydrogen, an alkali metal atom, ammonium or a cation formed from an amine, R and R' are each cyano; halogen; hydroxy; OR$_1$ or COOR$_1$ in which R$_1$ has its previous significance; nitro; linear or branched partially or completely fluorinated $C_1$–$C_8$-alkyl; NR$_3$R$_4$ in which R$_3$ and R$_4$ are the same or different and each is hydrogen or linear or branched $C_1$–$C_{12}$-alkyl; —N$^{\oplus}$R$_1$R$_3$R$_4$ in which R$_1$, R$_3$ and R$_4$ have their previous significance or linear or branched $C_1$–$C_8$-alkylene-R$_2$ in which R$_2$ is OR$_1$, COOR$_1$ or NR$_3$R$_4$, R$_5$ and R$_6$ are each independently from the other hydrogen; linear or branched $C_1$–$C_4$-alkyl; unsubstituted aryl or aryl which is substituted by cyano, halogen, OR$_1$ or COOR$_1$, nitro, linear or branched $C_1$–$C_8$-alkyl, NR$_3$R$_4$ in which R$_3$ and R$_4$ are the same or different and each is hydrogen or linear or branched $C_1$–$C_{12}$-alkyl; —N$^{\oplus}$R$_1$R$_3$R$_4$ in which R$_1$, R$_3$ and R$_4$ have their previous significance or linear or branched $C_1$–$C_8$-alkylene-R$_2$ in which R$_2$ is OR$_1$, COOR$_1$ or NR$_3$R$_4$, with the proviso that each n is 1, if R and R' are both $C_1$–$C_4$-alkyl.

2. A process according to claim 1 in which from 1.5 to 75 mg, per liter of wash liquor, of one or more compounds having the formula (1) or (2) is introduced into the wash liquor.

3. A process according to claim 1 in which the anion A is halide, perchlorate, sulphate, nitrate, hydroxide, BF$_4^-$, PF$_6^-$ or a carboxylate.

4. A process according to claim 3 in which the halide anion A is chloride.

5. A process according to claim 3 in which the carboxylate anion A is acetate, triflate or tosylate.

6. A process according to claim 1 in which Y is —[C(R$_8$)$_2$]$_2$ wherein R$_8$ is hydrogen or methyl, —CX=CX— in which X is cyano, —(CH$_2$)$_q$—NR$_8$—(CH$_2$)$_q$— in which R$_8$ has its previous significance and q is 1, 2, 3 or 4; or a 1,2-cyclohexylene or phenylene residue having the formula:

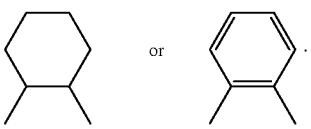

7. A process according to claim 1 in which R and R' are dimethylamino, diethylamino, hydroxy, methoxy, ethoxy, chloro or nitro.

8. A process according to claim 1 in which when n is 1, the group R or R' is in the 4-position of the respective benzene ring, with the exceptions that when R or R' is nitro or CO$_2$R$_2$, the group R or R' is in the 5-position of the respective benzene ring.

9. A process according to claim 1 in which when n is 2, the groups R or R' are in the 4,6-positions of the respective benzene ring, with the exceptions that when R or R' is nitro or CO$_2$R$_2$ the groups R or R' are in the 3,5-positions of the respective benzene ring.

10. A process according to claim 1 in which R or R' is di-(C$_1$–C$_{12}$alkyl)amino.

11. A process according to claim 10 in which the alkyl moiety in the group di-(C$_1$–C$_{12}$alkyl)amino contains from 1 to 4 carbon atoms.

12. A process according to claim 1 in which the compound of formula (1) is one or more of the compounds of formulae:

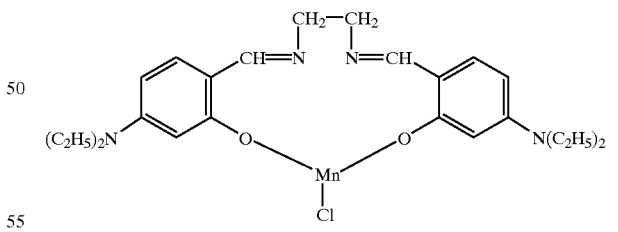

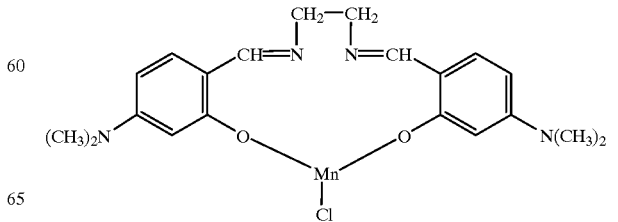

-continued
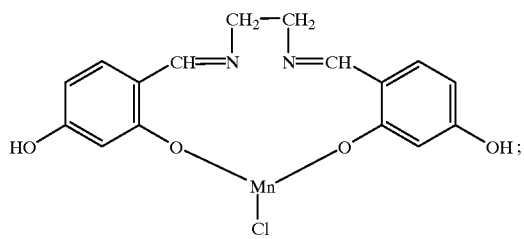
(1C)
and
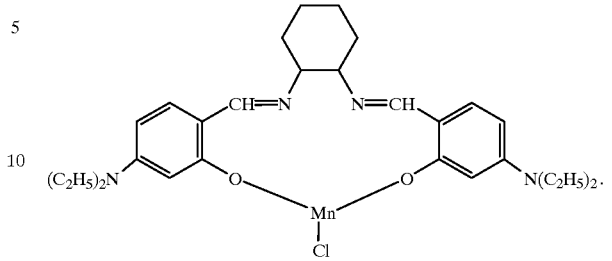
(1D)
* * * * *